United States Patent [19]

Kurmeier et al.

[11] Patent Number: 5,324,449

[45] Date of Patent: *Jun. 28, 1994

[54] SUBSTITUTED PHENYL TRIFLUOROMETHYL ETHERS

[75] Inventors: Hans-Adolf Kurmeier, Seeheim-Jugenheim, Fed. Rep. of Germany; Bernhard Scheuble, Yokohama, Japan; Eike Poetsch, Mühltal; Ulrich Finkenzeller, Plankstadt, both of Fed. Rep. of Germany

[73] Assignee: Merck Patent Gesellschaft mit beschrankter Haftung, Darmstadt, Fed. Rep. of Germany

[*] Notice: The portion of the term of this patent subsequent to Jun. 16, 2009 has been disclaimed.

[21] Appl. No.: 20,469

[22] PCT Filed: Sep. 5, 1988

[86] PCT No.: PCT/EP88/00804

§ 371 Date: May 24, 1989

§ 102(e) Date: May 24, 1989

[87] PCT Pub. No.: WO89/02884

PCT Pub. Date: Apr. 6, 1989

Related U.S. Application Data

[63] Continuation of Ser. No. 803,787, Dec. 6, 1991, abandoned, which is a continuation of Ser. No. 362,438, May 24, 1989, abandoned.

[30] Foreign Application Priority Data

Sep. 25, 1987 [DE] Fed. Rep. of Germany ....... 3732284

[51] Int. Cl.⁵ .................... C09K 19/52; C09K 19/34; C09K 19/30; C07C 43/225; C02F 1/13

[52] U.S. Cl. .................... 252/299.01; 252/299.61; 252/299.62; 252/299.63; 252/299.64; 252/299.65; 252/299.66; 252/299.67; 568/631; 568/645; 568/655; 568/661; 359/103

[58] Field of Search .......... 252/299.01, 299.1, 299.61, 252/299.62, 299.63, 299.64, 299.65, 299.66, 299.67; 359/103; 568/631, 642, 645, 655, 661, 663; 570/127

[56] References Cited

U.S. PATENT DOCUMENTS

| | | | |
|---|---|---|---|
| 3,506,718 | 4/1970 | Mutsch | 586/56 |
| 3,998,972 | 12/1976 | Farooq et al. | 586/56 |
| 4,048,235 | 9/1977 | Karrer | 586/631 |
| 4,393,231 | 7/1983 | Misaki et al. | 252/299.5 |
| 4,415,470 | 11/1983 | Eidenschink et al. | 252/299.63 |
| 4,512,636 | 4/1985 | Andrews et al. | 252/299.5 |
| 4,617,140 | 10/1986 | Eidenschink et al. | 252/299.61 |
| 4,630,897 | 12/1986 | Andrews et al. | 252/299.5 |

(List continued on next page.)

FOREIGN PATENT DOCUMENTS

| | | |
|---|---|---|
| 0193191 | 9/1986 | European Pat. Off. . |
| 0387032 | 9/1990 | European Pat. Off. . |
| 3511111 | 10/1986 | Fed. Rep. of Germany . |
| 3906040 | 9/1989 | Fed. Rep. of Germany . |
| 55-157523 | 12/1980 | Japan . |
| 58-18326 | 2/1983 | Japan . |
| 88/08441 | 11/1988 | PCT Int'l Appl. . |
| 2162515 | 2/1986 | United Kingdom . |

OTHER PUBLICATIONS

*Titov et al., Mol. Cryst. Liq. Cryst., vol. 47, pp. 1–5 (1978).

Rieger et al., "Bulk Resistivity of Liquid Crystals and their RC-Time Constant in Displays," Presentation No. 16 at Freiburger Arbeidstagung 1989, Conference Proceedings, Frieburg (1989).

Finkenzeller et al., "Physical Properties of Liquid Crystals: III. Dielectric Permittivities," Liquid Crystal Newsletter 4, Merck (1989).

*Primary Examiner*—Shean Wu
*Attorney, Agent, or Firm*—Millen, White, Zelano & Branigan

[57] ABSTRACT

Substituted phenyl trifluoromethyl ethers of the formula I $$R^1-(A^1-Z^1)_n-A^2-Z^2-A^3-OCF_3 \qquad I$$

in which $R^1$, $A^1$, $Z^1$, n, $A^2$, $Z^2$ and $A^3$ have the meaning given in claim 1, are suitable as components of liquid-crystalline phases.

16 Claims, No Drawings

U.S. PATENT DOCUMENTS

| | | | |
|---|---|---|---|
| 4,678,811 | 7/1987 | Franke et al. | 514/721 |
| 4,709,030 | 11/1987 | Petrzilka et al. | 252/399.61 |
| 4,726,911 | 2/1988 | Krause et al. | 252/299.61 |
| 4,822,519 | 4/1989 | Saito et al. | 252/299.61 |
| 4,871,470 | 10/1989 | Wächtler et al. | 252/299.63 |
| 4,874,545 | 10/1989 | Heppke | 252/299.61 |
| 4,877,548 | 10/1989 | Kitano et al. | 252/299.63 |
| 4,880,562 | 11/1989 | Kitano et al. | 252/299.63 |
| 4,886,619 | 12/1989 | Jamilis | 252/299.1 |
| 4,886,620 | 12/1989 | Hopf et al. | 252/299.61 |
| 4,886,621 | 12/1989 | Sage et al. | 252/299.61 |
| 4,911,863 | 3/1990 | Sage et al. | 252/299.65 |
| 5,032,313 | 7/1991 | Goto et al. | 252/299.63 |
| 5,045,229 | 9/1991 | Bartmann et al. | 252/299.01 |
| 5,082,587 | 1/1992 | Janulis | 252/299.01 |
| 5,122,295 | 6/1992 | Weber et al. | 252/299.01 |
| 5,122,297 | 6/1992 | Reiffenrath et al. | 252/299.63 |
| 5,171,469 | 12/1992 | Hittich et al. | 252/299.01 |

SUBSTITUTED PHENYL TRIFLUOROMETHYL ETHERS

This application is a continuation of application Ser. No. 07803,787, filed Dec. 6, 1991 now abandoned which is a continuation of Ser. No. 07/362,438 filed May 24, 1989 based PCT/EP88/00804 filed Sep. 5, 1988 now abandoned.

SUMMARY OF THE INVENTION

The invention relates to substituted phenyl trifluoromethyl ethers of the formula I $$R^1-(A^1-Z^1)_n-A^2-Z^2-A^3-OCF_3 \quad\quad I$$

in which $R^1$ is H or alkyl having 1-18 C atoms in which one or more $CH_2$ groups may also be replaced by —E—, —O—, —S— and/or —CO—, where two heteroatoms are not linked directly to one another, or perfluoroalkyl having 1-18 C atoms in which one or more $CF_2$ groups may also be replaced by —$CH_2$—, —E—, —O—, —S— and/or —CO—, where two heteroatoms are not linked directly to one another, is CH=CX, CX=CH, C≡C, CHY,

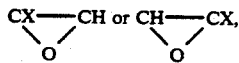

X is Y, $CH_3$ or H,
P is CN, NCS, NCO or halogen,
$A^1$ and $A^2$, independently of one another, are each 1,4-cyclohexylene, in which one or two non-adjacent $CH_2$ groups may also be replaced by —O— and/or S atoms, 1,4-cyclohexenylene, 1,4-bicyclo(2.2.2)octylene, piperidine-1,4-diyl or 1,4-phenylene, in which one or more CH groups may be replaced by N, which is unsubstituted or monosubstituted or polysubstituted by halogen atoms and/or CN and/or $CH_3$ groups,
$Z^1$ and $Z^2$ are each —CO—O—, —O—CO—, —$CH_2$O—, —$OCH_2$—, —$CH_2CH_2$—, —CH=CH— or a single bond,
$A^3$ is a 1,4-phenylene group which is unsubstituted or monosubstituted or polysubstituted by halogen atoms and/or CN and/or $CH_3$ groups
and
n is 0, 1 or 2, with the proviso that $Z^2$ is —$CH_2O$—, —$OCH_2$—, —$CH_2CH_2$—, —CH=CH— or a single bond in the case where n=0 or 1 $R^1$=alkoxy and $A^1$=$A^2$=$A^3$=unsubstituted 1,4-phenylene, and to the use thereof as components in liquid-crystalline phases.

For reasons of simplicity below, Cyc is a 1,4-cyclohexylene group, Che is a 1,4-cyclohexenylene group, Dio is a 1,3-dioxane-2,5-diyl group, Dit is a 1,3-dithiane-2,5-diyl group, Phe is a 1,4-phenylene group, Pyd is a pyridine-2,5-diyl group, Pyr is a pyrimidine-2,5-diyl group and Bi is a bicyclo(2,2,2)octylene group, where Cyc and/or Phe may be unsubstituted or substituted by one or more halogen atoms and/or $CH_3$ groups and/or CN groups.

The compounds of the formula I can be used as components in liquid-crystalline phases, in particular for displays which are based on the principle of the twisted cell, the guest/host effect, the effect of deformation of aligned phases or the effect of dynamic scattering.

The invention had the object of discovering novel stable liquid-crystalline or mesogenic compounds which are suitable as components of liquid-crystalline phases and, in particular, have comparatively low viscosity and relatively high dielectric anisotropy.

It has now been found that compounds of the formula I are highly suitable as components of liquid-crystalline phases. In particular, they have comparatively low viscosities. They can be used to obtain stable liquid-crystalline phases having a broad mesophase range and advantageous values for optical and dielectrical anisotropy.

In addition, the provision of compounds of the formula I considerably extends, very generally, the range of liquid-crystalline substances which are suitable, from various applicational points of view, for the production of liquid-crystalline mixtures.

The compounds of the formula I have a broad field of application. Depending on the choice of substituents, these compounds can be used as base materials of which liquid-crystalline phases are predominantly composed, or compounds of the formula I can be added to liquid-crystalline base materials made of other classes of compounds in order, for example, to influence the dielectrical and/or optical anisotropy of a dielectric of this type and/or to optimize its threshold voltage and/or its viscosity.

The compounds of the formula I are colourless in the pure state and form liquid-crystalline mesophases in a temperature range which is favourable for electrooptical use. They are stable chemically, thermally and against light.

The invention thus relates to the compounds of the formula I and to the use of these compounds as components of liquid-crystalline phases. The invention furthermore relates to liquid-crystalline phases containing at least one compound of the formula I and to liquid-crystal display elements, in particular electrooptical display elements, which contain such phases.

Above and below, $R^1$, $A^1$, $Z^1$, n, $A^2$, $Z^2$ and $A^3$ have the meaning indicated, unless expressly stated otherwise.

The compounds of the formula I accordingly cover compounds containing two rings of the sub-formulae Ia and Ib:

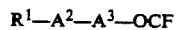   Ia

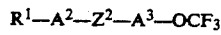   Ib compounds containing three rings of the sub-formulae Ic to If:

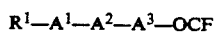   Ic

   Id

   Ie

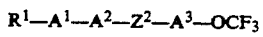   If and compounds containing four rings of the sub-formulae Ig to In:

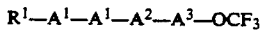   Ig

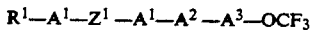   Ih

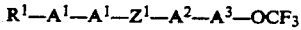   Ii

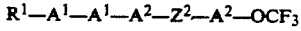   Ij

R$^1$—A$^1$—Z$^1$—A$^1$—Z$^1$—A$^2$—A$^3$—OCF$_3$  Ik

R$^1$—A$^1$—Z$^1$—A$^1$—A$^2$—Z$^2$—A$^3$—OCF$_3$  Il

R$^1$—A$^1$—A$^1$—Z$^1$—A$^2$—Z$^2$—A$^3$—OCF$_3$  Im

R$^1$—A$^1$—Z$^1$—A$^1$—Z$^1$—A$^2$—Z$^2$—A$^3$—OCF$_3$  In

Of these, those of the sub-formulae Ia, Ib, Ic, Id, Ie, If, Ih, Ij and Il are particularly preferred.

The preferred compounds of the sub-formula Ia cover those of the sub-formulae Iaa to Iaf:

R$^1$—Phe—Phe—OCF$_3$  Iaa

R$^1$—Dio—Phe—OCF$_3$  Iab

R$^1$—Pyr—Phe—OCF$_3$  Iac

R$^1$—Pyd—Phe—OCF$_3$  Iad

R$_1$—Cyc—Phe—OCF$_3$  Iae

R$_1$—Che—Phe—OCF$_3$  Iaf

Of these, those of the formulae Iaa, Iab, Iad and Iae are particularly preferred.

The preferred compounds of the sub-formula Ib cover those of the sub-formulae Iba to Ibl:

R$^1$—Phe—CH$_2$CH$_2$—Phe—OCF$_3$  Iba

R$^1$—Phe—OCH$_2$—Phe—OCF$_3$  Ibb

R$^1$—Cyc—CH$_2$CH$_2$—Phe—OCF$_3$  Ibc

R$^1$—Cyc—OCO—Phe—OCF$_3$  Ibd

R$^1$—A$^2$—CH$_2$CH$_2$—Phe—OCF$_3$  Ibe

R$^1$—A$^2$—CH$_2$O—Phe—OCF$_3$  Ibf

R$^1$—A$^2$—OCH$_2$—Phe—OCF$_3$  Ibg

R$^1$—A$^2$—COO—Phe—OCF$_3$  Ibh

R$^1$—A$^2$—OCO—Phe—OCF$_3$  Ibi

R$^1$—Che—CH$_2$CH$_2$—Phe—OCF$_3$  Ibj

R$_1$—Phe—OCO—Phe—OCF$_3$  Ibk

R$^1$—Cyc—COO—Phe—OCF$_3$  Ibl

The preferred compounds of the sub-formula Ic cover those of the sub-formulae Ica to Ici:

R$^1$—Phe—Phe—Phe—OCF$_3$  Ica

R$^1$—Phe—Dio—Phe—OCF$_3$  Icb

R$_1$—Cyc—Cyc—Phe—OCF$_3$  Icc

R$^1$—Pyd—Phe—Phe—OCF$_3$  Icd

R$^1$—Pyr—Phe—Phe—OCF$_3$  Ice

R$^1$—Cyc—Phe—Phe—OCF$_3$  Icf

R$^1$—Dio—Phe—Phe—OCF$_3$  Icg

R$^1$—Che—Phe—Phe—OCF$_3$  Ich

R$^1$—Phe—Che—Phe—OCF$_3$  Ici

Of these, those of the formulae Icc and Icf are particularly preferred.

The preferred compound of the sub-formula Id cover those of the sub-formula Ida to Idk:

R$^1$—Phe—Z$^1$—Phe—Z$^2$—Phe—OCF$_3$  Ida

R$^1$—Phe—Z$^1$—Dio—Z$^2$—Phe—OCF$_3$  Idb

R$^1$—Cyc—Z$^1$—Cyc—Z$^2$—Phe—OCF$_3$  Idc

R$^1$—Pyd—Z$^1$—Phe—Z$^2$—Phe—OCF$_3$  Ide

R$^1$—Phe—Z$^1$—Pyd—Z$^2$—Phe—OCF$_3$  Idf

R$^1$—Pyr—Z$^1$—Phe—Z$^2$—Phe—OCF$_3$  Idg

R$^1$—Phe—Z$^1$—Pyr—Z$^2$—Phe—OCF$_3$  Idh

R$^1$—Phe—Z$^1$—Cyc—Z$^2$—Phe—OCF$_3$  Idi

R$^1$—Dio—Z$^1$—Phe—Z$^2$—Phe—OCF$_3$  Idj

R$^1$—Che—Z$^1$—Phe—Z$^2$—Phe—OCF$_3$  Idk

The preferred compounds of the sub-formula Ie cover those of the sub-formulae Iea to Iei:

R$^1$—Pyr—Z$^1$—Phe—Phe—OCF$_3$  Iea

R$^1$—Dio—Z$^1$—Phe—Phe—OCF$_3$  Ieb

R$^1$—Cyc—Z$^1$—Phe—Phe—OCF$_3$  Iec

R$^1$—Phe—Z$^1$—Cyc—Phe—OCF$_3$  Ied

R$^1$—Cyc—Z$^1$—Cyc—Phe—OCF$_3$  Iee

R$^1$—Phe—Z$^1$—Dio—Phe—OCF$_3$  Ief

R$^1$—Pyd—Z$^1$—Phe—Phe—OCF$_3$  Ieg

R$^1$—Phe—Z$^1$—Pyr—Phe—OCF$_3$  Ieh

R$^1$—Phe—Z$^1$—Che—Phe—OCF$_3$  Iei

The preferred compounds of the sub-formula If cover those of the sub-formulae Ifa to Ifm:

R$^1$—Pyr—Phe—Z$^2$—Phe—OCF$_3$  Ifa

R$^1$—Pyr—Phe—OCH$_2$—Phe—OCF$_3$  Ifb

R$^1$—Phe—Phe—Z$^2$—Phe—OCF$_3$  Ifc

R$^1$—Cyc—Cyc—Z$^2$—Phe—OCF$_3$  Ifd

R$^1$—Cyc—Cyc—CH$_2$CH$_2$—Phe—OCF$_3$  Ife

R$^1$—Pyd—Phe—Z$^2$—Phe—OCF$_3$  Iff

R$^1$—Dio—Phe—Z$^2$—Phe—OCF$_3$  Ifg

R$^1$—Phe—Cyc—Z$^2$—Phe—OCF$_3$  Ifh

R$^1$—Phe—Pyd—Z$^2$—Phe—OCF$_3$  Ifi

R$^1$—Che—Phe—Z$^2$—Phe—OCF$_3$  Ifj

R$^1$—Phe—Che—Z$^2$—Phe—OCF$_3$  Ifk

R$^1$—Pyr—Phe—CH$_2$CH$_2$—Phe—OCF$_3$  Ifl

R¹—Cyc—Phe—CH₂CH₂—Phe—OCF₃   Ifm

The preferred compounds of the sub-formulae Ig to In cover those of the sub-formulae Io to Iv:

R¹—Cyc—Cyc—Phe—Phe—OCF₃   Io

R¹—A¹—CH₂O—A¹—A²—Phe—OCF₃   Ip

R¹—Cyc—Cyc—Z¹—A²—Phe—OCF₃   Iq

R¹—A¹—A¹—A²—CH₂CH₂—Phe—OCF₃   Ir

R¹—Phe—Z¹—CH₂CH₂—Phe—OCF₃   Is

R¹—Phe—Z¹—Phe—Phe—Z²—Phe—OCF₃   It

R¹—A¹—COO—A¹—COO—A²—Phe—OCF₃   Iu

R¹—A¹—A¹—COO—A²—Z²—Phe—OCF₃   Iv

In the compounds of the formulae above and below, R¹ is preferably alkyl, furthermore alkoxy. A¹ and A² are preferably Phe, Cyc, Che, Pyd, Pyr or Dio. The compounds of the formula I preferably contain no more than one of the radicals Bi, Pyd, Pyr, Dio and Dit.

R¹ is preferably also an alkyl group in which two adjacent CH₂ groups have been replaced by —O— and —CO— or —CO— and —O—. Furthermore, R¹ is preferably an alkyl group in which one CH₂ group has been replaced by —C|C— or —CH=CH—.

Preferred compounds of the formula I and of all the sub-formulae are also those in which A¹ and/or A² is (are) 1,4-phenylene which is substituted by one or more F atoms.

Z¹ and Z² are preferably single bonds, and secondarily preferably —CH₂CH₂—, —CH₂O— or —OCH₂—. Furthermore the groups —COO—, —OCO— or —CH=CH— are preferred for Z¹ and Z².

A³ is preferably a 1,4-phenylene group which is unsubstituted or substituted by one or two F atoms.

The following compounds of the formulae 1 to 13 are particularly preferred of the laterally substituted compounds:

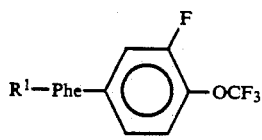
1

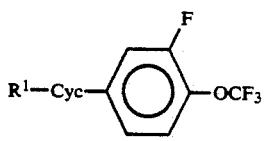
2

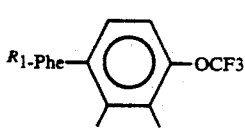
3

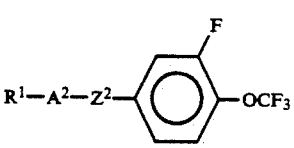
4

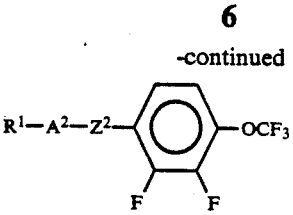
5

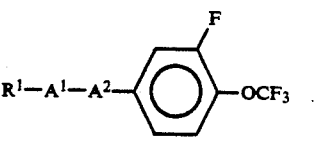
6

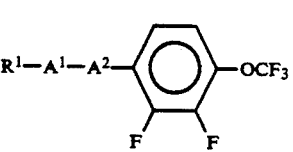
7

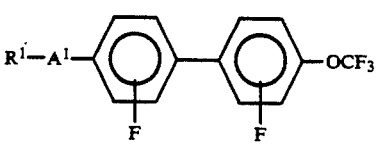
8

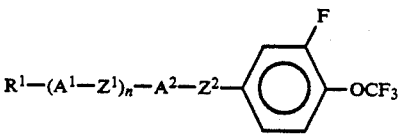
9

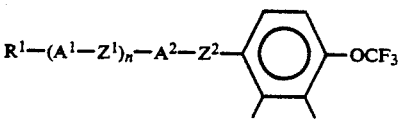
10

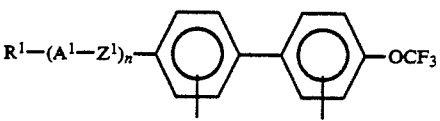
11

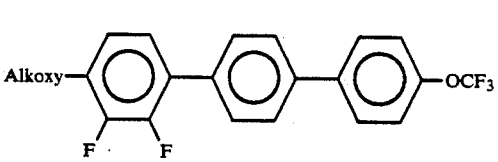
12

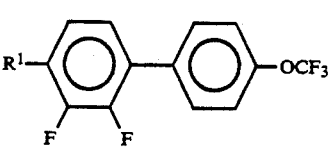
13

If R¹ is an alkyl radical or an alkoxy radical, it may be straight-chain or branched. It is preferably straight-chain, has 2, 3, 4, 5, 6, 7, 8 or 9 C atoms and is accordingly preferably ethyl, propyl, butyl, pentyl, hexyl, heptyl, octyl, nonyl, ethoxy, propoxy, butoxy, pentoxy, hexyloxy, heptyloxy, octyloxy or nonyloxy, furthermore also methyl, methoxy, decyl, undecyl, dodecyl, tridecyl, tetradecyl, decyloxy, undecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

If $R^1$ is an alkyl radical in which a $CH_2$ group is replaced by —CH=CH—, it may be straight-chain or branched. It is preferably straight-chain and has 2 to 10 C atoms. It is accordingly preferably vinyl, prop-1- or —2—enyl but—1—, —2— or 3-enyl, pent-1-, -2- -3- or 4-enyl, hex-1-, -2-, -3-, Compounds of the formula I having a branched wing group $R^1$ may occasionally be important due to better solubility in the customary liquid-crystalline base materials, but in particular as chiral dopes if they are optically active. Compounds of the formula I having $S_A$ phases are suitable for thermally addressed displays.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4methylhexyl, 2-nonyl, 2-decyl, 2-dodecyl, 6-methyloctoxy, 6-methyloctanoyloxy, 5-methylheptyloxycarbonyl, 2methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

Formula I covers the racemates of the compounds and the optical antipodes, and mixtures thereof.

In the formula I, $R^1$ is furthermore alternatively perfluoroalkyl preferably having 2, 3, 4, 5, 6, 7, 8 or 9 C atoms.

Of these compounds of the formula and of the sub-formulae, those are preferred in which at least one of the radicals present therein has one of the preferred meanings indicated.

In the compounds of the formula I, preferred stereoisomers are those which the Cyc and piperidine rings are trans-1,4-disubstituted. Those of the abovementioned formulae which contain one or more Pyd, Pyr and/or Dio groups in each case include the two 2,5 positional isomers.

The 1,4-cyclohexenylene group preferably has the following structures:

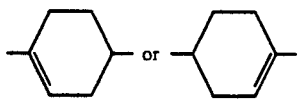

The compounds of the formula I are prepared by methods known per se, as described in the literature (for example in the standard works such as Houben-Weyl, Methoden der Organischen Chemie, [Methods of Organic Chemistry], Georg-Thieme-Verlag, Stuttgart, Vol. IX, pp. 867 ff.), namely under the reaction conditions which are known and suitable for the reactions mentioned. Variants which are known per se, but not described here in greater detail, can also be used here.

If desired, the s tarring materials can also be formed in situ in a manner such that they are not isolated from the reaction mixture but instead reacted further to form the compounds of the formula I.

Thus, compounds of the formula I can be prepared by reducing a compound which otherwise corresponds to the formula I, but contains one or more reducible groups and/ or C-C bonds in place of H atoms.

Suitable reducible groups are preferably carbonyl groups, in particular keto groups, furthermore, for example, free or esterified hydroxyl groups or aromatically bound halogen atoms. Preferred starting materials for the reduction correspond to the formula I, but contain a cyclohexene ring or cyclohexanone ring in place of a cyclohexane ring and/or a —CH=CH— group in place of a —$CH_2CH_2$— group and/or a —CO— group in place of a —$CH_2$— group and/or a free or functionally derived (for example in the form of its p-toluenesulfonate) OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid or a hydrocarbon, such as cyclohexane. Suitable catalysts are expediently noble metals, such as Pt or Pd, which can be employed in the form of oxides (for example $PrO_2$ or PdO), on a support (for example Pd on charcoal, calcium carbonate or strontium carbonate) or in finely divided form.

Ketones can also be reduced by the method of Clemmensen (using zinc, amalgamated zinc or tin and hydrochloric acid, expediently in aqueous alcoholic solution or in the heterogeneous phase with water/toluene at temperatures between about 80° and 120°) or by the method of Wolff-Kishner (using hydrazine, expediently in the presence of alkali, such as KOH or NaOH, in a high-boiling solvent, such as diethylene glycol or triethylene glycol, at temperatures between about 100° and 200°) to form the corresponding compounds of the formula I, which contain alkyl groups and/or —$CH_2CH_2$— bridges.

In addition, reductions using complex hydrides are possible, for example, arylsulfonyloxy groups can be reductively removed using $LiAlH_4$, and in particular p-toluenesulfonyloxymethyl groups can be reduced to methyl groups, expediently in an inert solvent, such as diethyl ether or THF, at temperatures between about 0° and 100°. Double bonds can be hydrogenated using $NaBH_4$ or tributyltin hydride in methanol.

Esters of the formula I can also be obtained by esterification of corresponding carboxylic acids (or reactive derivatives thereof) using alcohols or phenols (or reactive derivatives thereof).

The appropriate carboxylic acids and alcohols or phenols are known and can be prepared analogously to known processes.

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1–4 C atoms in the alkyl group.

Suitable reactive derivatives of the alcohols or phenols mentioned are, in particular, the corresponding metal alkoxides or phenoxides, preferably of an alkali metal, such as sodium or potassium.

The esterification is advantageously carried out in the presence of an inert solvent. In particular, ethers, such as diethyl ether, di-n-butyl ether, THF, dioxane or anisole, ketones, such as acetone, butanone or cyclohexanone, amides such as DMF or hexamethylphosphoric triamide, hydrocarbons, such as benzene, toluene or xylene, halogenated hydrocarbons, such as carbon tetrachloride or tetrachloroethylene, and sulfoxides, such as dimethyl sulfoxide or sulfolane, are highly suitable.

In order to prepare nitriles of the formula I (in which $A^1$, $A^2$ and/or $A^3$ is substitued by at least one CN group), appropriate acid amides, for example those in which a $CONH_2$ group is present in place of the CN radical, can be dehydrated. The amides can be obtained, for example, from the corresponding esters or acyl halides by reaction with ammonia. Suitable dehydrating agents are, for example, inorganic acid chlorides, such as $SOCl_2$, $PCl_3$, $PCl_5$, $POCl_3$, $SO_2Cl_2$, $COCl_2$ and further $P_2O_5$, $P_2S_5$ and $AlCl_3$ (for example as a double compound with NaCl), aromatic sulfonic acids and sulfonyl halides. This reaction can be carried out in the presence or absence of an inert solvent at temperatures between about 0° and 150°; suitable solvents are, for example, bases, such as pyridine or triethylamine, aromatic hydrocarbons, such as benzene, toluene or xylene, or amides, such as DMF.

In order to prepare the abovementioned nitriles of the formula I, it is also possible to react appropriate acid halides, preferably the chlorides, with sulfamide, expediently in an inert solvent, such as tetramethylene sulfone, at temperatures between about 80° and 150°, presulfone, at 120°. After customary work-up, the nitriles can be isolated directly.

Ethers of the formula I (in which R is an alkoxy group and/or $Z^1$ and/or $Z^2$ is an $-OCH_2-$ or $-CH_2O-$ group) can be obtained by etherification of the corresponding hydroxyl compounds, preferably the corresponding phenols, the hydroxyl compound expediently first being converted into an appropriate metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide alkylsulfonate or dialkyl sulfate, expediently in an inert solvent, such as acetone, 1,2-dimethoxyethane, DMF or dimethyl sulfoxide, or alternatively an excess of aqueous or aqueous alcoholic NaOH or KOH at temperatures between about 20° and 100°.

In order to prepare nitriles of the formula I (in which $A^1$, $A^2$ and/or $A^3$ is substituted by at least one CN group), it is also possible to react corresponding chlorine or bromine compounds of the formula I (in which $A^1$ and/or $A^2$ and/or $A^3$ is substituted by at least one Cl or Br atom) with a cyanide, expediently with a metal cyanide, such as NaCN, KCN or $Cu_2(CN)_2$, for example in the presence of pyridine in an inert solvent, such as DMF or N-methylpyrrolidone, at temperatures between 20° and 200°.

Compounds of the formula I in which $A^1$, $A^2$ and/or $A^3$ is substituted by at least one F or Cl atom and/or a CN group can also be obtained from the corresponding diazonium salts by replacement of the diazonium group by a fluorine or chlorine atom or by a CN group, for example by the method of Schiemann or Sandmeyer.

Dioxane derivatives or dithiane derivatives of the formula I (in which one of the $A^1$ and/or $A^2$ groups is a 1,3-dioxane-2,5-diyl group or a 1,3-dithiane-2,5-diyl group) are expediently prepared by reacting a corresponding aldehyde (or a reactive derivative thereof) with an appropriate 1,3-diol (or a reactive derivative thereof) or an appropriate 1,3-dithiol, preferably in the presence of an inert solvent, such as benzene or toluene, and/or in the presence of a catalyst, for example a strong acid, such as sulfuric acid, benzenesulfonic acid or p-toluenesulfonic acid at temperatures between about 20° and about 150°, preferably between about 80° and 120°. Suitable reactive derivatives of the starting materials are primarily acetals.

Some of the aldehydes and 1,3-diols or 1,3-dithiols mentioned, and the reactive derivatives thereof, are known and some can be prepared without difficulties by standard methods of organic chemistry from compounds known from the literature. For example, the aldehydes can be obtained by oxidation of the corresponding alkyls or by reduction of the corresponding carboxylic acids or derivatives thereof, and the diols can be obtained by reduction of the corresponding diesters and the dithiols by reaction of the corresponding dihalides with NaSH.

When preparing the compounds of the formula I, it is particularly advantageous to start from starting compounds which already contain the $-OCF_3$ group, for example p-trifluoromethoxybenzaldehyde or 1-bromo-4-trifluoromethoxybenzene. A person s killed in the art can obtain further possible preparations from the literature mentioned or from the Examples.

The liquid-crystalline phases according to the invention comprise 2 to 25, preferably 3 to 15, components, including at least one compound of the formula I. The other components are selected from nematic or nematogenic substances, in particular the known substances from the classes comprising the azoxybenzenes, benzylideneanilines, biphenyls, terphenyls, phenyl or cyclohexylbenzoates, phenyl or cyclohexyl cyclohexanoates, phenyl cyclohexanes, cyclohexylbiphenyls, cyclohexylcyclohexanes, cyclohexylnapthalenes, 1,4-biscyclohexylbenzenes, 4,4'-biscyclohexylbiphenyls, phenyl- or cyclohexylpyrimidines, phenyl- or cyclohexyldioxanes, phenyl- or cyclohexyldithianes, 1,2-bisphenylethanes, 1,2-biscyclohexylethanes, 1-phenyl-2-cyclohexylethanes, optionally halogenated stilbenes, benzyl phenyl ethers, tolanes and substituted cinnamic acids.

The most important compounds which are suitable as components of liquid-crystalline phases of this type may be characterized by the formula II $$R^1-L-G-E-R^2 \qquad II$$

in which L and E are each a carbocyclic or heterocyclic ring system from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthaline, di- and tetraydronaphthaline, quinazoline and tetrahydroquinazoline, G is

| G is | $-CH=CH-$ | $-N(O)=N-$ |
|---|---|---|
| | $-CH=CY-$ | $-CH=N(O)-$ |
| | $-C\equiv C-$ | $-CH_2-CH_2-$ |
| | $-CO-O-$ | $-CH_2-O-$ |
| | $-CO-S-$ | $-CH_2-S-$ |
| | $-CH=N-$ | $-COO-Phe-COO-$ | a C—C single bond, Y is halogen, preferably chlorine or —CN, and $R^1$ and $R^2$ are alkyl, alkanoyloxy or alkoxycarbonyloxy having up to 18, preferably up to 8, carbon atoms, or one of these radicals is altenatively CN, NO2, $CF_3$, F, Cl or Br. In most of these compounds, $R^1$ and $R^2$ are different from one another, one of these radicals usually being an alkyl or alkoxy group. However, other variants of the proposed substituents are common. Many such substances or mixtures thereof are commercially available. All these substances can be prepared by methods known from the literature.

The liquid-crystalline phases according to the invention contain about 0.1 to 99, preferably 10 to 95%, of one or more compounds of the formula I. Further preferred liquid-crystalline phases are those which contain 0.1–50, in particular 0.5–30,% of one or more compounds of the formula I. It is also possible to use isotropic compounds of the formula I in the phases according to the invention.

The liquid-crystalline phases according to the invention are produced in a manner which is known per se. In general, the components are dissolved in one another, expediently at elevated temperature.

By means of suitable additives, the liquid-crystalline phases according to the invention can be modified so that they can be used in all types of liquid-crystal display elements which have been disclosed hitherto.

Such additives are known to those skilled in the art and described in detail in the literature. For example, conductive salts, preferably ethyldimethyldodecylammonium 4-hexyloxybenzoate, tetrabutylammonium tetraphenylboranate or complex salts of crown ethers (cf., for example, I. Haller et al., Mol. Cryst. Liq. Cryst., volume 24, pages 249–258 (1973)) can be added in order to improve the conductivity, dichroic dyes in order to produce coloured guest/host systems or substances in order to change the dielectric anisotropy, the viscosity and/or the orientation of the nematic phases. Such substances are described, for example, in DE-OS 2,209,127, 2,240,864, 2,321,632, 2,338,281, 2,450,088, 2,637,430, 2,853,728 and 2,902,177.

EXAMPLES

The examples below are intended to illustrate the invention without representing any limitation. Above and below, percentages mean per cent by weight. All temperatures are given in degrees Celsius. m.p. means melting point, c.p.=clear point. Furthermore, C=crystalline state, N=nematic phase, S=smectic phase and I=isotropic phase. The figures between these symbols are the transition temperatures.

EXAMPLE 1

0.1 mol of p-trifluoromethoxybenzaldehyde, 0.1 mol of ethylpropanediol and 0.2 g of p-toluenesulfonic acid are refluxed for 2 hours in 100 ml of toluene. After evaporation of the solvent, vacuum distillation and subsequent crystallization, trifluoromethoxy-4-(5-ethyl-1,3-dioxan-2-yl)benzene of m.p.=31° and c.p. (extr.)=−90° is obtained.

The following are prepared analogously: Trifluoromethoxy-4-(5-propyl-1,3-dioxan-2-yl )benzene, m.p. 36.3°, c.p. 35°
Trifluoromethoxy-4-(5-butyl-1,3-dioxan-2-yl)benzene
Trifluoromethoxy-4-(5-pentyl-1,3-dioxan-2-yl)benzene, m.p. 23°, c.p. 36°
Trifluoromethoxy-4-(5-hexyl-1,3-dioxan-2-yl)benzene
Trifluoromethoxy-4-(5-heptyl-1,3-dioxan-2-yl)benzene
Trifluoromethoxy-4-(5-octyl-1,3-dioxan-2-yl)benzene
Trifluoromethoxy-4-(5-nonyl-1,3-dioxan-2-yl)benzene
Trifluoromethoxy-4-(5-decyl-1,3-dioxan-2-yl)benzene
Trifluoromethoxy-4-[5-(trans-4-ethylcyclohexyl)-1,3-dioxan-2-yl]benzene
Trifluoromethoxy-4-[5-(trans-4-propylcyclohexyl)-1,3-dioxan-2-yl]benzene
Trifluoromethoxy-4-[5-(trans-4-butylcyclohexyl)-1,3-dioxan-2-yl]benzene
Trifluoromethoxy-4-[5-(trans-4-pentylcyclohexyl)-1,3-dioxan-2-yl]benzene, C 67° $S_B$ 146° N 150.5° I
Trifluoromethoxy-4-[5-(trans-4-hexylcyclohexyl)-1,3-dioxan-2-yl]benzene
Trifluoromethoxy-4-[5-(trans-4-heptylcyclohexyl)-1,3-dioxan-2-yl]benzene

EXAMPLE 2

2 mol of anhydrous hydrofluoric acid are transferred into an autoclave which has been cooled to 0°. A mixture of 0.18 mol of tetrachloromethane and 0.06 mol of 4-(trans-4-ethylcyclohexyl)phenol is then added. The mixture is stirred for about 8 hours at 150°, cooled, poured into ice water and washed with ether. The two phases are stirred for about 30 minutes and separated, and the ether solution is washed with 5% KOH until alkaline. After drying, filtering off, distilling off and purification, trifluoromethoxy-4-(trans-ethylcyclo-hexyl)benzene is obtained.

The following are prepared analogously:
Trifluoromethoxy-4-(trans-4-propylcyclohexyl)benzene
Trifluoromethoxy-4-(trans-4-butylcyclohexyl)benzene
Trifluoromethoxy-4-(trans-4-pentylcyclohexyl)benzene
Trifluoromethoxy-4-(trans-4-hexylcyclohexyl)benzene
Trifluoromethoxy-4-(trans-4-heptylcyclohexyl)benzene
Trifluoromethoxy-4-(trans-4-octylcyclohexyl)benzene
Trifluoromethoxy-4-(trans-4-nonylcyclohexyl)benzene
Trifluoromethoxy-4-(trans-4-decylcyclohexyl)benzene

EXAMPLE 3

0.42 g of lithium and 3.5 g of $ZnBr_2$ are added to a mixture of 8.6 g of trans-4-(trans- 4-propylcyclo-hexyl)-cyclohexyl bromide and 50 ml of the THF/toluene (1:4) at 0°. The reaction solution is treated with ultrasound for 3 hours at 0°–10°. After addition of 7.4 g of 1-bromo-4-(trifluoromethoxy)benzene and 0.44 g of 1,1-bis(diphenylphosphino)-ferrocene-palladium (II) dichloride [$PdCl_2$ (dppf)], the mixture is stirred at room temperature for 24 hours, poured into 25 ml of water (+5 ml of 1 N HCl) and stirred for 15 minutes, the organic phase is separated off, and the aqueous phase is extracted with toluene.

After work-up of the organic phases and purification by chromatography and/or crystallization, trifluoromethoxy-4-[trans-4-(trans-4-propylcyclohexyl)-cyclohexyl]benzene is obtained, C 39° S 68° N148.6° I.

The following are prepared analogously:
Trifluoromethoxy-4-[trans-4-(trans-4-ethylcyclohexyl)-cyclohexyl]benzene
Trifluoromethoxy-4-[trans-4-(trans-4-butylcyclohexyl)-cyclohexyl]benzene
Trifluoromethoxy-4-[trans-4-(trans-4-pentylcyclohexyl)cyclohexyl]benzene
Trifluoromethoxy-4-[trans-4-(trans-4-hexylcyclohexyl)-cyclohexyl]benzene
Trifluoromethoxy-4-[trans-4-(trans-4-heptylcyclohexyl)cyclohexyl]benzene Trifluoromethoxy-4-[trans-4-(trans-4-octylcyclohexyl)-benzene Trifluoromethoxy-4-[trans-4-(trans-4-nonylcyclohexyl)cyclohexyl]benzene Trifluoromethoxy-4-[trans-4-(trans-4-decylcyclohexyl)cyclohexyl]benzene

EXAMPLE 4

By etherification of 50 mmol of trifluoromethoxy-p-hydroxymethylbenzene with 50 mmol of 2-(p-hydroxybenzene)5-nonylpyrimidine in 150 ml of THF in the presence of 55 mmol of triphenylphosphine and 55 mmol of diethyl azodi-carboxylate, 4-(5-nonylpyrimidin-2-yl)-phenyl p-trifluoro-methoxybenzyl ether of m.p.=56° and c.p.=155° is obtained.

The following are obtained analogously:

4-(5-Ethylpyrimidin-2-yl)phenyl p-trifluoromethoxybenzyl ether 4-(5-Methylpyrimidin-2-yl)phenyl p-trifluoromethoxybenzyl ether 4-(5-Propylpyrimidin-2-yl)phenyl p-trifluoromethoxybenzyl ether 4-(5-Butylpyrimidin-2-yl)phenyl p-trifluoromethoxybenzyl ether 4-(5-Pentylpyrimidin-2-yl)phenyl p-trifluoromethoxybenzyl ether 4-(5-Hexylpyrimidin-2-yl)phenyl p-trifluoromethoxybenzyl ether 4-(5-Heptylpyrimidin-2-yl)phenyl p-trifluoromethoxybenzyl ether 4-(5-Octylpyrimidin-2-yl)phenyl p-trifluoromethoxybenzyl ether

EXAMPLE 5

Equimolar amounts of p-trifluoromethoxybenzimidamide hydrochloride (can be prepared from the corresponding nitrile via the corresponding ethyl benzimidate hydrochloride and heptylmalondialdehyde bis-diethyl acetal are heated at 150° for 15 hours. After cooling, the residue is dissolved in ethanol. Customary work-up gives 2-(p-trifluoromethoxybenzene)-5-heptylpyrimidine of m.p. 23° and c.p. 34°.

The following are prepared analogously:
2-(p-Trifluoromethoxybenzene)-5-ethylpyrimidine
2-(p-Trifluoromethoxybenzene)-5-propylpyrimidine
2-(p-Trifluoromethoxybenzene)-5-butylpyrimidine
2-(p-Trifluoromethoxybenzene)-5-pentylpyrimidine
2-(p-Trifluoromethoxybenzene)-5-hexylpyrimidine
2-(p-Trifluoromethoxybenzene)-5-methoxypyrimidine
2-(p-Trifluoromethoxybenzene)-5-ethoxypyrimidine
2-(p-Trifluoromethoxybenzene)-5-propoxypyrimidine
2-(p-Trifluoromethoxybenzene)-5-butoxypyrimidine
2-(p-Trifluoromethoxybenzene)-5-pentyloxypyrimidine
2-(p-Trifluoromethoxybenzene)-5-hexyloxypyrimidine
2-(p-Trifluoromethoxybenzene)-5-heptyloxypyrimidine

EXAMPLE 6 a) 95 g of trifluoromethoxybenzaldehyde in 150 ml of THF are added over the course of 2-3 hours at −10° to −5° to a mixture of 300 g of trans-4-(trans-4-propylcyclohexyl)cyclohexylmethyltriphenylphosphonium iodide, 56 g of potassium tert.-butoxide and 500 ml of THF. The mixture is allowed to warm to room temperature and neutralized using 2 N HCl, water is added, and the mixture is extracted with methyl tert.-butyl ether. After work-up of the organic phase and purification by chromatography on silica gel, 1-(4-trifluoromethoxyphenyl)-2-[trans-4-(trans-4-propylcyclohexyl)cyclohexyl]ethene is obtained.

b) 162 g of the ethene derivative are hydrogenated at room temperature and atmospheric pressure in 800 ml of THF over 40 g of 5 % Pd/C. After work-up and purification by crystallization, 1-(4-trifluoromethoxyphenyl)-2[trans-4-(trans-4-propylcyclohexyl)-cyclohexyl]ethane having C 24° C. 60° $S_G$ 76° N 133.7° I is obtained.

The following are prepared analogously:
1-(4-Trifluoromethoxyphenyl)-2-[trans-4-(trans-4-ethylcyclohexyl)cyclohexyl]ethane
1-(4-Trifluoromethoxyphenyl)-2-[trans-4-(trans-4-butylcyclohexyl)cyclohexyl]ethane
1-(4-Trifluoromethoxyphenyl)-2-[trans-4-(trans-4-pentylcyclohexyl)cyclohexyl]ethane, C44° $S_B$ 108° N130° I
1-(4-Trifluoromethoxyphenyl)-2-[trans-4-(trans-4-hexylcyclohexyl)cyclohexyl]ethane
1-(4-Trifluoromethoxyphenyl)-2-[trans-4-(trans-4-heptylcyclohexyl)cyclohexyl]ethane

EXAMPLE 7

15.5 g of 1-bromo-4-(trans-4-pentylcyclohexyl)benzene in 50 ml of THF are added to a boiling mixture of 1.2 g of magnesium and 25 mL of THF. When the addition is complete, the mixture is heated for a further 1 hour, cooled and added to a solution of 6.7 g of $ZnBr_2$ in 50 ml of THF at 0°–15°. After stirring for 1 hour, 12.3 g of 1-bromo-4-(trifluoromethoxy)benzene and 0.75 g of $PdCl_2$ (dppf) are added. The mixture is stirred at 5° for 15 minutes and then at room temperature for 24 hours. The mixture is poured onto 100 ml of saturated $NH_4Cl$ solution, and the organic phase is separated off and extracted with toluene. After work-up of the organic phase and purification by chromatography and/or crystallization, trifluoro-methoxy-4-[4-(trans-4-pentylcyclohexyl)phenyl]benzene, 43° $S_B$ 128° N 147.4° I is obtained.

The following are prepared analogously:
Trifluoromethoxy-4-[4-(trans-4-ethylcyclohexyl)phenyl]benzene
Trifluoromethoxy-4-[4-(trans-4-propylcyclohexyl)phenyl]benzene
Trifluoromethoxy-4-[4-(trans-4-butylcyclohexyl)phenyl]benzene
Trifluoromethoxy-4-[4-(trans-4-hexylcyclohexyl)phenyl]benzene
Trifluoromethoxy-4-[4-(trans-4-heptylcyclohexyl)phenyl]benzene
Trifluoromethoxy-4-[4-(trans-4-octylcyclohexyl)phenyl]benzene
Trifluoromethoxy-4-[4-(trans-4-nonylcyclohexyl)phenyl]benzene
Trifluoromethoxy-4-[4-(trans-4-decylcyclohexyl)phenyl]benzene
Trifluoromethoxy-2-fluoro-4-[4-(trans-4-ethylcyclohexyl)phenyl]benzene
Trifluoromethoxy-2-fluoro-4-[4-(trans-4-propylcyclohexyl)phenyl]benzene
Trifluoromethoxy-2-fluoro-4-[4-(trans-4-butylcyclohexyl)phenyl]benzene
Trifluoromethoxy-2-fluoro-4-[4-(trans-4-pentylcyclohexyl)phenyl]benzene
Trifluoromethoxy-2-fluoro-4-[4-(trans-4-hexylcyclohexyl)phenyl]benzene
Trifluoromethoxy-2-fluoro-4-[4-(trans-4-heptylcyclohexyl)phenyl]benzene Trifluoromethoxy-2-fluoro-4-[4-(trans-4-octylcyclohexyl)phenyl]benzene
Trifluoromethoxy-2-fluoro-4-[4-(trans-4-nonylcyclohexyl)phenyl]benzene
Trifluoromethoxy-2-fluoro-4-[4-(trans-4-decylcyclohexyl)phenyl]benzene.

EXAMPLE 8

Analogously to Example 7, from 4-bromo-4'-pentylbiphenyl and trifluoromethoxy-4-bromobenzene, the corresponding trifluoromethoxy-4-(4'-pentylbiphenyl-4-yl)benzene is obtained.

The following are prepared analogously:
Trifluoromethoxy-4-(4'-ethylbiphenyl-4-yl)benzene
Trifluoromethoxy-4-(4'-propylbiphenyl-4-yl)benzene
Trifluoromethoxy-4-(4'-butylbiphenyl-4-yl)benzene
Trifluoromethoxy- 4-(4'-hexylbiphenyl-4-yl)benzene
Trifluoromethoxy- 4-(4'-heptylbiphenyl-4-yl)benzene
Trifluoromethoxy- 4-(4'-octylbiphenyl-4-yl)benzene
Trifluoromethoxy-2-fluoro-4-(4'-ethylbiphenyl-4-yl)benzene
Trifluoromethoxy-2-fluoro-4-(4'-propylbiphenyl-4yl)benzene
Trifluoromethoxy-2-fluoro-4-(4'-butylbiphenyl-4-yl)benzene
Trifluoromethoxy-2-fluoro-4-(4'-pentylbiphenyl-4-yl)benzene
Trifluoromethoxy-2-fluoro-4-(4'-hexylbiphenyl-4-yl)benzene
Trifluoromethoxy-2-fluoro-4-(4'-heptylbiphenyl-4-yl)benzene
Trifluoromethoxy-2-fluoro-4-(4'-octylbiphenyl-4-yl)benzene
Trifluoromethoxy-4-(2',3'-difluoro-4'-ethoxybiphenyl-4-yl)-benzene
Trifluoromethoxy-4-(2',3'-difluoro-4'-propoxybiphenyl-4-yl)-benzene
Trifluoromethoxy-4-(2',3'-difluoro-4'-butoxybiphenyl-4-yl)-benzene
Trifluoromethoxy-4-(2',3'-difluoro-4'-pentyloxybiphenyl-4-yl)-benzene
Trifluoromethoxy-4-(2',3'-difluoro-4'-hexyloxybiphenyl-4-yl)-benzene
Trifluoromethoxy-4-(2',3'-difluoro-4'-ethylbiphenyl-4-yl)-benzene
Trifluoromethoxy-4-(2',3'-difluoro-4'-propylbiphenyl-4-yl)-benzene
Trifluoromethoxy-4-(2',3'-difluoro-4'-butylbiphenyl-4-yl)-benzene
Trifluoromethoxy-4-(2',3'-difluoro-4'-pentylbiphenyl-4-yl)-benzene
Trifluoromethoxy-4-(2',3'-difluoro-4'-hexylbiphenyl-4-yl)-benzene
Trifluoromethoxy-4-(2',3'-difluoro-4'-heptylbiphenyl-4-yl)-benzene

EXAMPLE 9

37 ml of butyllithium (15% in hexane) are added at −75° to a mixture of 12 g of 2-ethoxy-5-bromopyridine and 50 ml of THF, and the mixture is stirred for a further 1 hour. 7.5 g of $ZnBr_2$ in 25 ml of THF are subsequently added at −70° to −65°, and the mixture is again stirred for 1 hour. 14.5 g of trifluoromethoxy-4-bromobenzene in 25 ml of THF and 1 g of $PdCl_2$ (dppf) are then added. The temperature is allowed to rise to room temperature, and the mixture is then stirred for 16 hours. Work-up is effected analogously to Example 7, and 2-ethoxy-5-(4-trifluoromethoxyphenyl)pyridine having C 36° $S_A$ ((33° )I is obtained after purification by chromatography and/or crystallization.

The following are prepared analogously:
2-Methoxy-5-(4-trifluoromethoxyphenyl)pyridine
2-Propoxy-5-(4-trifluoromethoxyphenyl)pyridine
2-Butoxy-5-(4-trifluoromethoxyphenyl)pyridine
2-Pentyloxy-5-(4-trifluoromethoxyphenyl)pyridine
2-Hexyloxy-5-(4-trifluoromethoxyphenyl)pyridine
2-Heptyloxy-5-(4-trifluoromethoxyphenyl)pyridine
2-Octyloxy-5-(4-trifluoromethoxyphenyl)pyridine
2-Methyl-5-(4-trifluoromethoxyphenyl)pyridine
2-Ethyl-5-(4-trifluoromethoxyphenyl)pyridine
2-Propyl-5-(4-trifluoromethoxyphenyl)pyridine
2-Butyl-5-(4-trifluoromethoxyphenyl)pyridine
2-Pentyl-5-(4-trifluoromethoxyphenyl)pyridine
2-Hexyl-5-(4-trifluoromethoxyphenyl)pyridine
2-Heptyl-5-(4-trifluoromethoxyphenyl)pyridine
2-Octyl-5-(4-trifluoromethoxyphenyl)pyridine

EXAMPLE 10

Analogously to Example 9, by reacting 14.0 g of 2-(4-bromophenyl)-5-propylpyrimidine and 12.1 g of trifluoromethoxy-4-bromobenzene, the corresponding 2-(4'-trifluoromethoxybiphenyl-4-yl)-5-propylpyrimidine having C 125° $S_G$ 1110 $S_A$ 218° I is obtained.

The following are prepared analogously:
2-(4'-Trifluoromethoxybiphenyl-4-yl)-5-methylpyrimidine
2-(4'-Trifluoromethoxybiphenyl-4-yl)-5-ethylpyrimidine
2-(4'-Trifluoromethoxybiphenyl-4-yl)-5-butylpyrimidine
2-(4'-Trifluoromethoxybiphenyl-4-yl)-5-pentylpyrimidine
2-(4'-Trifluoromethoxybiphenyl-4-yl)-5-hexylpyrimidine
2-(4'-Trifluoromethoxybiphenyl-4-yl)-5-heptylpyrimidine
2-(4'-Trifluoromethoxybiphenyl-4-yl)-5-octylpyrimidine
2-(4'-Trifluoromethoxybiphenyl-4-yl)-5-methoxypyrimidine
2-(4'-Trifluoromethoxybiphenyl-4-yl)-5-ethoxypyrimidine
2-(4'-Trifluoromethoxybiphenyl-4-yl)-5-propoxypyrimidine
2-( 4'-Trifluoromethoxybiphenyl-4-yl)-5-butoxypyrimidine
2-( 4'-Trifluoromethoxybiphenyl-4-yl)-5-pentyloxypyrimidine
2-( 4'-Trifluoromethoxybiphenyl-4-yl)-5-hexyloxypyrimidine
2-( 4'-Trifluoromethoxybiphenyl-4-yl)-5-heptyloxypyrimidine
2-( 4'-Trifluoromethoxybiphenyl-4-yl)-5-octyloxypyrimidine.

EXAMPLE 11 a) A mixture of 2.8 g of 4-(5-heptylpyrimidin-2-yl)styrene, 3.7 g of trifluoromethoxy-4-bromobenzene, 1.4 ml of triethylamine, 25 ml of acetonitrile, 50 mg of Pd(II) acetate and 125 mg of tri-o-tolylphosphine is refluxed for 36 hours. After cooling, the mixture is evaporated and, after purification by chromatography, 1-(4-trifluoromethoxyphenyl)-2-[4-(5-heptylpyrimidin-2-yl)phenyl]ethene having C 123° $S_c$ 151° $S_A$ 242° I is obtained.

b) This vinyl compound is hydrogenated at room temperature and atmospheric pressure in THF using pd (5% on C). After work-up and purification by chromatography and/or crystallization, 1-(4-trifluoromethoxyphenyl)-2-[4-(5-heptylpyrimidin-2-yl)phenyl]ethane having C 63° S$_B$ 98° S$_A$ 144° I is obtained.

The following are prepared analogously:

1-(4-Trifluoromethoxyphenyl)-2-[4-(5-ethylpyrimidin-2-yl)phenyl]ethane 1-(4-Trifluoromethoxyphenyl)-2-[4-(5-propylpyrimidin-2-yl)phenyl]ethane 1-(4-Trifluoromethoxyphenyl)-2-[4-(5-butylpyrimidin-2-yl)phenyl]ethane 1-(4-Trifluoromethoxyphenyl)-2-[4-(5-pentylpyrimidin-2-yl)phenyl]ethane 1-(4-Trifluoromethoxyphenyl)-2-[4-(5-hexylpyrimidin-2-yl)phenyl]ethane 1-(4-Trifluoromethoxyphenyl)-2-[4-(5-octylpyrimidin-2-yl)phenyl]ethane 1-(4-Trifluoromethoxyphenyl)-2-[4-(5-ethoxypyrimidin-2-yl)phenyl]ethane 1-(4-Trifluoromethoxyphenyl)-2-[4-(5-propoxypyrimidin-2-yl)phenyl]ethane 1-(4-Trifluoromethoxyphenyl)-2-[4-(5-butoxypyrimidin-2-yl)phenyl]ethane 1-(4-Trifluoromethoxyphenyl)-2-[4-(5-pentyloxypyrimidin-2-yl)phenyl]ethane 1-(4-Trifluoromethoxyphenyl)-2-[4-(5-hexyloxypyrimidin-2-yl)phenyl]ethane 1-(4-Trifluoromethoxyphenyl)-2-[4-(5-heptyloxypyrimidin-2-yl)phenyl]ethane 1-(4-Trifluoromethoxyphenyl)-2-[4-(5-octyloxypyrimidin-2-yl)phenyl]ethane

EXAMPLE 12 a) A mixture of 25.7 g of 4-(trans-4-pentylcyclohexyl)styrene, 14.5g of 4-(trifluoromethoxy)-iodobenzene, 100 ml of acetonitrile, 7 ml of triethylamine, 0.23 g or Pd(II) acetate and 0.6 g of tri-o-tolylphosphine is heated at the boiling point for 24 hours. After cooling to 0°, filtering off the precipitated substance with suction, and washing with acetonitrile and water, 1-(4-trifluoromethoxyphenyl)-2-[4-(trans-4-pentylcyclohexyl) phenyl]-ethene having C 72° S$_B$ 168° S$_A$ 194° N 224.1° I, is obtained after purification by crystallization from ethanol/ethyl acetate.

b) The ethene derivative from a) is hydrogenated in THF using Pd/C at room temperature and atmospheric pressure. After work-up and purification by crystallization, 1-(4-trifluoromethoxyphenyl)-2-[4-(trans-4-pentylcyclohexyl)phenyl]-ethane is obtained.

The following are prepared analogously:

1-(4-Trifluoromethoxyphenyl)-2-[4-(trans-4-methylcyclohexyl)phenyl]-ethane 1-(4-Trifluoromethoxyphenyl)-2-[4-(trans-4-ethylcyclohexyl)phenyl]-ethane 1-(4-Trifluoromethoxyphenyl)-2-[4-(trans-4-propylcyclohexyl)phenyl]-ethane 1-(4-Trifluoromethoxyphenyl)-2-[4-(trans-4-butylcyclohexyl)phenyl]-ethane 1-(4-Trifluoromethoxyphenyl)-2-[4-(trans-4-pentylcyclohexyl)phenyl]-ethane 1-(4-Trifluoromethoxyphenyl)-2-[4-(trans-4-hexylcyclohexyl)phenyl]-ethane 1-(4-Trifluoromethoxyphenyl)-2-[4-(trans-4-heptylcyclohexyl)phenyl]-ethane

EXAMPLE 13

A Grignard compound is prepared from 1.2 g of magnesium, 50 ml of THF and 11.4 g of 4-pentylbromobenzene in 25 ml of THF. When the addition is complete, the mixture is refluxed for a further 1 hour and cooled to 10°, and 14 g of 4-trifluoromethoxybromobenzene in 25 ml of THF and 0.73 g of PdCl$_2$ (dppf) are added. The cooling is removed, but the reaction mixture should not climb above 20°. The mixture is subsequently stirred at room temperature for 16 hours, poured into 100 ml of saturated NH$_4$Cl solution and stirred for a further 15 minutes, and the organic phase is then worked up. After purification by crystallization, trifluoromethoxy-4-(4-pentylphenyl)benzene having C 67° I is obtained.

The following are prepared analogously:

Trifluoromethoxy -4-(4-methylphenyl)benzene
Trifluoromethoxy -4-(4-ethylphenyl)benzene
Trifluoromethoxy -4-(4-propylphenyl)benzene
Trifluoromethoxy -4-(4-butylphenyl)benzene
Trifluoromethoxy -4-(4-hexylphenyl)benzene
Trifluoromethoxy -4-(4-heptylphenyl)benzene
Trifluoromethoxy -4-(2,3-difluoro-4-methylphenyl)benzene
Trifluoromethoxy -4-(2,3-difluoro-4-ethylphenyl)benzene
Trifluoromethoxy -4-(2,3-difluoro-4-propylphenyl)benzene
Trifluoromethoxy -4-(2,3-difluoro-4-butylphenyl)benzene
Trifluoromethoxy -4-(2,3-difluoro-4-pentylphenyl)benzene
Trifluoromethoxy -4-(2,3-difluoro-4-ethoxyphenyl)benzene
Trifluoromethoxy -4-(2,3-difluoro-4-methoxyphenyl)benzene
Trifluoromethoxy -4-(2,3-difluoro-4-propoxyphenyl)benzene
Trifluoromethoxy -4-(2,3-difluoro-4-butoxyphenyl)benzene
Trifluoromethoxy -4-(2,3-difluoro-4-pentyloxyphenyl)benzene

EXAMPLE 14

By reacting 7.5 g of 4-ethoxystyrene with 14.4 g of 4-trifluoromethoxyiodobenzene, 6.9 ml of triethylamine, 0.23 g of pd(II) acetate and 0.6 g of tri-o-tolylphosphine in 75 ml of acetonitrile, 1-(4-trifluoromethoxyphenyl)-2-(4-ethoxyphenyl)-ethene is obtained analogously to Example 12a).

The following are prepared analogously:

1-(4-Trifluoromethoxyphenyl)-2-(4-methoxyphenyl)-ethene 1-(4-Trifluoromethoxyphenyl)-2-(4-propoxyphenyl)-ethene 1-(4-Trifluoromethoxyphenyl)-2-(4-butoxyphenyl)-ethene 1-(4-Trifluoromethoxyphenyl)-2-(4-pentyloxyphenyl)-ethene 1-(4-Trifluoromethoxyphenyl)-2-(4-hexyloxyphenyl)-ethene 1-(4-Trifluoromethoxyphenyl)-2-(4-heptyloxyphenyl)-ethene 1-(4-Trifluoromethoxyphenyl)-2-(4-methylphenyl)-ethene 1-(4-Trifluoromethoxyphenyl)-2-(4-ethylphenyl)-ethene 1-(4-Trifluoromethoxyphenyl)-2-(4-propylphenyl)-ethene
1-(4-Trifluoromethoxyphenyl)-2-(4-butylphenyl)-ethene
1-(4-Trifluoromethoxyphenyl)-2-(4-pentylphenyl)-ethene
1-(4-Trifluoromethoxyphenyl)-2-(4-hexylphenyl)-ethene
1-(4-Trifluoromethoxyphenyl)-2-(4-heptylphenyl)-ethene
1-(4-Trifluoromethoxyphenyl)-2-(4-octylphenyl)-ethene

EXAMPLE 15

By hydrogenation of the ethene derivatives, prepared in Example 14, using Pd/C in THF, the corresponding ethane derivatives are obtained:
1-(4-Trifluoromethoxyphenyl)-2-(4-ethoxyphenyl)-ethane
1-(4-Trifluoromethoxyphenyl)-2-(4-methoxyphenyl)-ethane
1-(4-Trifluoromethoxyphenyl)-2-(4-propoxyphenyl)-ethane
1-(4-Trifluoromethoxyphenyl)-2-(4-butoxyphenyl)-ethane
1-(4-Trifluoromethoxyphenyl)-2-(4-pentyloxyphenyl)-ethane
1-(4-Trifluoromethoxyphenyl)-2-(4-hexyloxyphenyl)-ethane
1-(4-Trifluoromethoxyphenyl)-2-(4-heptyloxyphenyl)-ethane
1-(4-Trifluoromethoxyphenyl)-2-(4-methylphenyl)-ethane
1-(4-Trifluoromethoxyphenyl)-2-(4-ethylphenyl)-ethane
1-(4-Trifluoromethoxyphenyl)-2-(4-propylphenyl)-ethane
1-(4-Trifluoromethoxyphenyl)-2-(4-butylphenyl)-ethane
1-(4-Trifluoromethoxyphenyl)-2-(4-pentylphenyl)-ethane
1-(4-Trifluoromethoxyphenyl)-2-(4-hexylphenyl)-ethane
1-(4-Trifluoromethoxyphenyl )-2-(4-heptylphenyl)-ethane
1-(4-Trifluoromethoxyphenyl )-2-(4-octylphenyl)-ethane
1-(4-Trifluoromethoxyphenyl)-2-(2,3-difluoro-4-ethoxyphenyl)-ethane
1-(4-Trifluoromethoxyphenyl)-2-(2,3-difluoro-4-propoxyphenyl)-ethane
1-(4-Trifluoromethoxyphenyl)-2-(2,3-difluoro-4-butoxyphenyl)-ethane
1-(4-Trifluoromethoxyphenyl)-2-(2,3-difluoro-4-pentyloxyphenyl)-ethane
1-(4-Trifluoromethoxyphenyt)-2-(2,3-difluoro-4-ethylphenyl)-ethane
1-(4-Trifluoromethoxyphenyl)-2-(2,3-difluoro-4-propylphenyl)-ethane
1-(4-Trifluoromethoxyphenyl)-2-(2,3-difluoro-4-butylphenyl)-ethane
1-(4-Trifluoromethoxyphenyl)-2-(2,3-difluoro-4-pentylphenyl)-ethane

EXAMPLE 16

0.7 g of lithium and 5.7 g of ZnBr$_2$ are added at 0° to a mixture of 15.4 g of trans-4-pentylcyclohexylethyliodide and 100 ml of THF/toluene (1:4), and the reaction mixture is treated with ultrasound at 0°–10° for 4 hours. 14.8 g of 4-trifluoromethoxybromobenzene and 0.88 g of PdCl$_2$ (dppf) are subsequently added at 5°. The mixture is allowed to warm to room temperature and is stirred for a further 16 hours. The mixture is then poured into 100 ml of saturated NH$_4$Cl solution, and the organic phase is work ed up. After purification by chromatography and/or crystallization, 1-(4-trifluoromethoxyphenyl)-2-(trans-4-pentylcyclohexyl)-ethane is obtained.

The following are prepared analogously:
1-(4-Trifluoromethoxyphenyl)-2-(trans-4-ethylcyclohexyl)ethane
1-(4-Trifluoromethoxyphenyl)-2-(trans-4-propylcyclohexyl)ethane
1-(4-Trifluoromethoxyphenyl)-2-(trans-4-butylcyclohexyl)ethane
1=(4-Trifluoromethoxyphenyl)-2-(trans-4-hexylcyclohexyl)ethane
1-(4-Trifluoromethoxyphenyl)-2-(trans-4-heptylcyclohexyl)ethane

EXAMPLE 17

Trifluoromethoxy-4-(trans-4-propylcyclohexyl)benzene is obtained analogously to Example 16 from 15.4 g of trans-4-propylcyclohexyl bromide and 18.2 g of 4-trifluoromethoxybromobenzene after purification by chromatography and/or vacuum distillation.

The following are prepared analogously:
Trifluoromethoxy-4-(trans-4-ethylcyclohexyl)benzene
Trifluoromethoxy-4-(trans-4-butylcyclohexyl)benzene
Trifluoromethoxy-4-(trans-4-pentylcyclohexyl)benzene
Trifluoromethoxy-4-(trans-4-hexylcyclohexyl)benzene
Trifluoromethoxy-4-(trans-4-heptylcyclohexyl)benzene
Trifluoromethoxy-4-(trans-4-octylcyclohexyl)benzene

EXAMPLE 18

First, 4.6 g of dicyclohexylcarbodiimide in 80 ml of toluene are added to a mixture of 4 g of 4-trifluoromethoxyphenol and 20 ml of toluene, 0.2 g of dimethylaminopyridine is then added, the mixture is stirred at room temperature for 1 hour, and 3.8 g of trans-4-ethylcyclohexanecarboxylic acid are then added. After work-up and purification by chromatography and/or crystallization, 4-(trifluoromethoxy)phenyl trans-4-ethylcyclohexanecarboxylate is obtained.

The following are prepared analogously:
4-(Trifluoromethoxy)phenyl trans-4-propylcyclohexanecarboxylate
4-(Trifluoromethoxy)phenyl trans-4-butylcyclohexanecarboxylate
4-(Trifluoromethoxy)phenyl trans-4-pentylcyclohexanecarboxylate
4-(Trifluoromethoxy)phenyl trans-4-hexylcyclohexanecarboxylate
4-(Trifluoromethoxy)phenyl trans-4-heptylcyclohexancarboxylate
4-( Trifluoromethoxy)phenyl trans-4-(trans-4-propylcyclohexyl)cyclohexanecarboxylate
4-( Trifluoromethoxy)phenyl trans-4-(trans-4-ethylcyclohexyl)cyclohexanecarboxylate
4-( Trifluoromethoxy)phenyl trans-4-(trans-4-butylcyclohexyl)cyclohexanecarboxylate
4-( Trifluoromethoxy)phenyl trans-4-(trans-4-pentylcyclohexyl)cyclohexanecarboxylate
4-( Trifluoromethoxy)phenyl trans-4-(trans-4-hexylcyclohexyl)cyclohexanecarboxylate 4-(Trifluoromethoxy)phenyl trans-4-(trans-4-heptylcyclohexyl)cyclohexanecarboxylate

EXAMPLE 19

10.0 g of dicyclohexylcarbodiimide in 20 ml of toluene are added with water cooling to a mixture of 9.1 g of 4-trifluoromethoxybenzoic acid, 6.0 g of 4-propylphenol, 2.7 g of dimethylaminopyridine and 30 ml of toluene. The mixture is stirred for 2 hours, 1 g of oxalic acid is added, and the mixture is stirred for a further hour and filtered with suction. The filtrate is washed by shaking with 1M HCl, the phases are separated, and the organic phase is washed by shaking with 1M NaOH and worked up. After purification by chromatography and/or crystallization, 4-propylphenyl 4-(trifluoromethoxy)benzoate having C 59° I is obtained.

The following are prepared analogously:
4-Ethylphenyl 4-(trifluoromethoxy)benzoate
4-Butylphenyl 4-(trifluoromethoxy)benzoate
4-pentylphenyl 4-(trifluoromethoxy)benzoate
4-Hexylphenyl 4-(trifluoromethoxy)benzoate
4-Heptylphenyl 4-(trifluoromethoxy)benzoate
4-Octylphenyl 4-(trifluoromethoxy)benzoate The examples below concern liquid-crystalline phases according to the invention:

EXAMPLE A

A liquid-crystalline phase, comprising
16% of p-trans-4-propylcyclohexylbenzonitrile,
4% of p-trans-4-pentylcyclohexylbenzonitrile,
9% of trifluoromethoxy-4-(5-propyl-1,3-dioxan-2-yl)benzene,
9% of trifluoromethoxy-4-(5-pentyl-1,3-dioxan-2-yl)benzene,
20% of trans-1-p-methoxyphenyl-4-propylcyclohexane,
11% of 4-ethyl-4'-(trans-4-propylcyclohexyl)biphenyl,
11% of 4-ethyl-4'-(trans-4-pentylcyclohexyl)biphenyl,
4% of 4,4'-bis-(trans-4-propylcyclohexyl)biphenyl,
6% of 4-(trans-4-pentylcyclohexyl)-4'-(trans-4-propylcyclohexyl)biphenyl,
3% of 4-(trans-4-propylcyclohexyl)-2'-fluoro-4'-(trans4-propylcyclohexyl)biphenyl,
4% of 2-fluoro-4-(trans-4-pentylcyclohexyl)-4'-(trans-4-propylcyclohexyl)biphenyl and
3% of 4-(trans-4-pentylcyclohexyl)-2'-fluoro-4'-(trans-4-pentylcyclohexyl)biphenyl, has a melting point of −17°, a clear point of 92° and a viscosity of 21 mm$^2$/s at 20°.

EXAMPLE B

A liquid-crystalline phase, comprising
8% of p-trans-4-propylcyclohexylbenzonitrile
12% of trifluoromethoxy-4-(5-propyl-1,3-dioxan-2-yl)benzene
10% of p-trans-4-butylcyclohexylbenzonitrile,
12% of trans-1-p-ethylphenyl-4-propylcyclohexane
6% of trans-1-p-methoxyphenyl-4-propylcyclohexane,
13% of 4-ethyl-4'-(trans-4-propylcyclohexyl)biphenyl,
12% of 4-ethyl-4'-(trans-4-pentylcyclohexyl)biphenyl,
3% of 4,4'-bis-(trans-4-propylcyclohexyl)biphenyl,
6% of 4-(trans-4-pentylcyclohexyl)-4'-(trans-4-propylcyclohexyl)biphenyl,
3% of 4,4'-bis-(trans-4-pentylcyclohexyl)biphenyl,
4% of 4-(trans-4-pentylcyclohexyl)-4'-(trans-4-propylcyclohexyl)biphenyl,
7% of 2-fluoro-4-(trans-4-pentylcyclohexyl)-4'-(trans4-propylcyclohexyl)biphenyl, and
4% of 4-(trans-4-pentylcyclohexyl)-2'-fluoro-4'-(trans4-pentylcyclohexyl)biphenyl, has a melting point of −20.8° clear point of 108° and a viscosity of 25 mm$^2$/s at 20°.

EXAMPLE C

A liquid-crystalline phase, comprising
7% of 2-p-cyanophenyl-5-propyl-1,3-dioxane,
6% of 2-p-cyanophenyl-5-butyl-1,3-dioxane,
4% of 2-p-cyanophenyl-5-pentyl-1,3-dioxane,
9% of trifluoromethoxy-4-(5-propyl-1,3-dioxan-2-yl)benzene
9% of trifluoromethoxy-4-(5-pentyl-1,3-dioxan-2-yl)benzene,
12% of 4-ethyl-4'-(trans-4-propylcyclohexyl)biphenyl,
10% of 4-ethyl-4'-(trans-4-pentylcyclohexyl)biphenyl,
5% of 2-p-pentyloxyphenyl-5-hexylpyrimidine,
5% of 2-p-hexyloxyphenyl-5-hexylpyrimidine,
5% of 2-p-heptyloxyphenyl-5-hexylpyrimidine,
4% of 2-p-propoxyphenyl-5-hexylpyrimidine,
4% of 2-p-heptyloxyphenyl-5-heptylpyrimidine,
4% of 2-p-nonyloxyphenyl-5-heptylpyrimidine,
7% of 2-fluoro-4-(trans-4-pentylcyclohexyl)-4'-(trans4-propyl cyclohexyl)biphenyl, and
9% of trans-1-p-methoxyphenyl-4-propylcyclohexane, has C-17° Sm 30° N 70° I.

EXAMPLE D

A liquid-crystalline phase comprising
20% of 1-(4-trifluoromethoxyphenyl)-2-[trans-4-(trans-4-propylcyclohexyl)cyclohexyl]-ethane
20% of 1-(4-trifluoromethoxyphenyl )-2-[trans-4-(trans-4-pentylcyclohexyl)cyclohexyl]-ethane
20% of trans-1-p-methoxyphenyl-4-propylcyclohexane,
20% of trans-1-p-ethoxyphenyl-4-propylcyclohexane and
20% of trans-1-p-butoxyphenyl-4-propylcyclohexane has a melting point of −6.2°, a clear point of 64° and a viscosity of 12 mm$^2$/s at 20°.

EXAMPLE E

A liquid-crystalline phase comprising
20% of p-trans-4-propylcyclohexyl-benzonitrile,
20% of trans-1-p-propylphenyl-4-pentylcyclohexane,
15% of trans-1-p-ethoxyphenyl-4-propylcyclohexane,
15% of trans-1-p-butoxyphenyl-4-propylcyclohexane,
15% of 4-trifluoromethoxy-4'-(trans-4-propylcyclohexyl)biphenyl and
15% of 4-trifluoromethoxy-4'-(trans-4-pentylcyclohexyl)biphenyl
has a clear point of 62°, a viscosity of 12 mm$^2$/s at 20° and Δn= +0.12.

EXAMPLE F

A liquid-crystalline phase comprising
10% of p-trans-4-propylcyclohexyl-benzonitrile,
10% of 2-p-cyanophenyl-5-propyl-1,3-dioxane,
10% of 4-propyl-4'-cyanobiphenyl, 10% of p-cyanophenyl-4-propylbenzoate,
10% of 3-fluoro-4-cyanophenyl-4-propylbenzoate
10% of trans- 1-p-methoxyphenyl-4-propylcyclohexane,
10% of trans- 1-p-ethoxyphenyl-4-propylcyclohexane,
15% of 4-ethyl-1-trans-4-(trans-4-propylcyclohexyl)-cyclohexyl-benzene and
15% of 4-trifluoromethoxy-1-trans-4-(trans-4-propylcyclohexyl)cyclohexyl-benzene
has a clear point of 66°, a viscosity of 22 mm$^2$/s and $\Delta n = +0.14$.

EXAMPLE G

A liquid-crystalline phase comprising
7% of 2-p-cyanophenyl-5-propyl-1,3-dioxane,
6% of 2-p-cyanophenyl-5-butyl-1,3-dioxane,
4% of 2-p-cyanophenyl-5-pentyl-1,3-dioxane,
9% of 1-(4-trifluoromethoxyphenyl)-2-[trans-4-(trans4-propylcyclohexyl)cyclohexyl]-ethane,
9% of 1-(4-trifluoromethoxyphenyl-2-[trans-4-(trans4-pentylcyclohexyl)cyclohexyl]-ethane,
12% of 4-ethyl-4'-(trans-4-propylcyclohexyl)-biphenyl,
10% of 4-ethyl-4'-(trans-4-pentylcyclohexyl)-biphenyl,
5% of 2-p-pentyloxyphenyl-5-hexylpyrimidine,
5% of 2-p-hexyloxyphenyl-5-hexylpyrimidine,
5% of 2-p-heptyloxyphenyl-5-hexylpyrimidine,
4% of 2-p-propoxyphenyl-5-hexylpyrimidine,
4% of 2-p-heptyloxyphenyl-5-heptylpyrimidine,
4% of 2-p-nonyloxyphenyl-5-heptylpyrimidine,
7% of 2-fluoro-4-(trans-4-pentylcyclohexyl)-4'-(trans-4-propylcyclohexyl)-biphenyl and
9% of trans-1-p-methoxyphenyl-4-propylcyclohexane has a melting point of −17°, a clear point of 99° and a viscosity of 32 mm$^2$/s 20°.

EXAMPLE H

A liquid-crystalline phase comprising
8% of p-trans-4-propylcyclohexyl-benzonitrile,
12% of 1-(4-trifluoromethoxyphenyl)-2-[trans-4-(trans-4-propylcyclohexyl)cyclohexyl]-ethane,
10% of p-trans-4-butylcyclohexyl-benzonitrile,
12% of trans-1-p-ethylphenyl-4-propylcyclohexane,
6% of trans-1-p-methoxyphenyl-4-propylcyclohexane,
13% of 4-ethyl-4'-(trans-4- propylcyclohexyl)-biphenyl,
12% of 4-ethyl-4'-(trans-4- pentylcyclohexyl)-biphenyl
3% of 4,4'-bis-(trans-4-propylcyclohexyl)-biphenyl,
6% of 4-(trans-4-pentylcyclohexyl)-4'-(trans-4-propylcyclohexyl)-biphenyl,
3% of 4,4'-bis-(trans-4-pentylcyclohexyl)-biphenyl,
4% of 4-(trans-4-pentylcyclohexyl)-4'-(trans-4-propylcyclohexyl)-biphenyl,
7% of 2 -fluoro-4-(trans-4-pentylcyclohexyl)-4'-(trans4-propylcyclohexyl)-biphenyl and
4% of 4 -(trans-4-pentylcyclohexyl)-2'-fluoro-4'-(trans4 -pentylcyclohexyl)-biphenyl has a melting point of −21°, a clear point of 123° and a viscosity of 27 mm$^2$/s at 20°.

EXAMPLE I

A liquid-crystalline phase comprising
16% of p-trans-4-propylcyclohexyl-benzonitrile,
4% of p- trans-4-pentylcyclohexyl-benzonitrile,
9% of 1-(4-trifluoromethoxyphenyl)-2-[trans-4-(trans-4-propylcyclohexyl)cyclohexyl]-ethane
9% of 1-(4-trifluoromethoxyphenyl)-2-[trans-4-(trans-4-pentylcyclohexyl)cyclohexyl]-ethane,
20% of trans-1-p-methoxyphenyl-4-propylcyclohexane,
11% of 4-ethyl-4'-(trans-4-propylcyclohexyl)-biphenyl,
11% of 4-ethyl-4'-(trans-4-pentylcyclohexyl)-biphenyl,
4% of 4,4'-bis-(trans-4-propylcyclohexyl)-biphenyl,
6% of 4-(trans-4-pentylcyclohexyl)-4'-(trans-4-propylcyclohexyl)-biphenyl,
3% of 4-(trans-4-propylcyclohexyl)-2'-fluoro-4'-(trans4-propylcyclohexyl)-biphenyl,
4% of 2- fluoro-4-(trans-4-pentylcyclohexyl)-4'-(trans-4'-propylcyclohexyl)-biphenyl and
3% of 4-(trans-4-pentylcyclohexyl)-2'-fluoro-4'-(trans4-pentylcyclohexyl)-biphenyl has a melting point of −15°, a clear point of 120° and a viscosity of 23 mm$^2$/s at 20°.

I claim:

1. A liquid-crystalline phase comprising at least two liquid crystalline components, wherein at least one component is a substituted phenyl trifluoromethyl ether of the formula I $$R^1-(A^1-Z^1)_n-A^2-Z^2-A^3-OCF_3 \qquad I$$

in which $R^1$ is alkyl having 1–18 C atoms in which one or more $CH_2$ groups may also be replaced by —E—, —O—, —S—and/or —CO—, where two heteroatoms are not linked directly to one another, or perfluoroalkyl having 1–18 C atoms in which one or more $CF_2$ groups may also be replaced by —$CH_2$—, —E—, —O—, —S— and/or —CO—, where two heteroatoms are not linked directly to one another, E is CH=CX, CX=CH, C≡C, CHY,

X is Y, $CH_3$ or H,
Y is CN, NCS, NCO or halogen,
$A^1$ and $A^2$, independently of one another, are each 1,4-cyclohexylene, in which one or two non-adjacent $CH_2$ groups may also be replaced by —O— and/or S atoms, 1,4-cyclohexenylene, 1,4-bicyclo(2.2.2)-octylene, piperidine-1,4-diyl or 1,4-phenylene, in which one or more CH groups may be replaced by N, which is unsubstituted or monosubstituted or polysubstituted by halogen atoms and-/or CN and/or $CH_3$ groups, [$Z^1$ and $Z^2$ are each —CO—O—, —O—CO—, —$CH_2$O—, —$OCH_2$, —$CH_2CH_2$—, —CH=CH— or a single bond,]
$Z^1$ is —$CH_2CH_2$—, —CH=CH— or a single bond,
$Z^2$ is —CO—O—, —$CH_2$O—, —$OCH_2$—, —$CH_2CH_2$—, —CH=CH— or a single bond,
$A^3$ is a 1,4-phenylene group which is unsubstituted or monosubstituted or polysubstituted by halogen atoms, CN, $CH_3$ or combination
and
n is 0, 1 or 2,
with the proviso that $Z^2$ is —$CH_2$O—, —$OCH_2$—, —$CH_2CH_2$—, —CH=CH— or a single bond in the case where n=0 or 1, $R^1$=alkoxy and $A^1$=$A^2$=$A^3$=unsubstituted 1,4-phenylene.

2. A liquid-crystal display element, comprising a liquid-crystalline phase according to claim 1.

3. An electrooptical display element, comprising as a dielectric, a liquid-crystalline phase according to claim 1.

4. A liquid-crystalline phase according to claim 1, comprising at least one substituted phenyl trifluoromethyl ether of the sub-formulae Ia and Ib:

$$R^1-A^2-A^3-OCF_3 \qquad Ia$$

$$R^1-A^2-Z^2-A^3-OCF_3 \qquad Ib$$

5. A liquid-crystalline phase according to claim 1, comprising at least one substituted phenyl trifluoromethyl ether of the sub-formulae Ic to If:

$$R^1-A^1-A^2-A^3-OCF_3 \qquad Ic$$

$$R^1-A^1-Z^1-A^2-Z^2-A^3-OCF_3 \qquad Id$$

$$R^1-A^1-Z^1-A^2-A^3-OCF_3 \qquad Ie$$

$$R^1-A^1-A^2-Z^2-A^3-OCF_3 \qquad If$$

6. A liquid-crystalline phase according to claim 1, comprising at least one substituted phenyl trifluoromethyl ether of the sub-formulae Ig to In:

$$R^1-A^1-A^1-A^2-A^3-OCF_3 \qquad Ig$$

$$R^1-A^1-Z^1-A^1-A^2-A^3-OCF_3 \qquad Ih$$

$$R^1-A^1-A^1-Z^1-A^2-A^3-OCF_3 \qquad Ii$$

$$R^1-A^1-A^1-A^2-Z^2-A^3-OCF_3 \qquad Ij$$

$$R^1-A^1-Z^1-A^1-Z^1-A^2-A^3-OCF_3 \qquad Ik$$

$$R^1-A^1-Z^1-A^1-A^2-Z^2-A^3-OCF_3 \qquad Il$$

$$R^1-A^1-A^1-Z^1-A^2-Z^2-A^3-OCF_3 \qquad Im$$

$$R^1-A^1-Z^1-A^1-Z^1-A^2-Z^2-A^3-OCF_3 \qquad In$$

7. A liquid-crystalline phase according to claim 1, comprising at least one substituted phenyl trifloromethyl ether of the sub-formulae Iaa to Iaf:

$$R^1-Phe-Phe-OCF_3 \qquad Iaa$$

$$R^1-Dio-Phe-OCF_3 \qquad Iab$$

$$R^1-Pyr-Phe-OCF_3 \qquad Iac$$

$$R^1-Pyd-Phe-OCF_3 \qquad Iad$$

$$R^1-Cyr-Phe-OCF_3 \qquad Iae$$

$$R^1-Che-Phe-OCF_3 \qquad Iaf$$

wherein Phe is a 1,4-phenylene group being unsubstituted or substituted by one or more halogen atoms or $CH_3$ or CN
Dio is a 1,3-dioxane-2,5-diyl group,
Pyd is a pyridine-2,5-diyl group,
Pyr is a pyrimidine-2,5-diyl group,
Cyc is a 1,4-cyclohexylene group and
Che is a 1,4-cyclohexenylene group.

8. A liquid-crystalline phase according to claim 4, comprising at least one substituted phenyl trifluoromethyl ether of the sub-formulae Iba to Ibl:

$$R^1-Phe-CH_2CH_2-Phe-OCF_3 \qquad Iba$$

$$R^1-Phe-OCH_2-Phe-OCF_3 \qquad Ibb$$

$$R^1-Cyc-CH_2CH_2-Phe-OCF_3 \qquad Ibc$$

$$R^1-A^2-CH_2CH_2-Phe-OCF_3 \qquad Ibe$$

$$R^1-A^2-CH_2O-Phe-OCF_3 \qquad Ibf$$

$$R^1-A^2-OCH_2-Phe-OCF_3 \qquad Ibg$$

$$R^1-A^2-COO-Phe-OCF_3 \qquad Ibh$$

$$R^1-Che-CH_2CH_2-Phe-OCF_3 \qquad Ibj$$

$$R^1-Cyc-COO-Phe-OCF_3 \qquad Ibl$$

wherein
Cyc is a 1,4-cyclohexylene group and
Che is a 1,4-cyclohexenylene group.

9. A liquid-crystalline phase according to claim 5, comprising at least one substituted phenyl trifluoromethyl ether of the sub-formulae Ica to Ici:

$$R^1-Phe-Phe-Phe-OCF_3 \qquad Ica$$

$$R^1-Phe-Dio-Phe-OCF_3 \qquad Icb$$

$$R^1-Cyc-Cyc-Phe-OCF_3 \qquad Icc$$

$$R^1-Pyd-Phe-Phe-OCF_3 \qquad Icd$$

$$R^1-Pyr-Phe-Phe-OCF_3 \qquad Ice$$

$$R^1-Cyc-Phe-Phe-OCF_3 \qquad Icf$$

$$R^1-Dio-Phe-Phe-OCF_3 \qquad Icg$$

$$R^1-Che-Phe-Phe-OCF_3 \qquad Ich$$

$$R^1-Phe-Che-Phe-OCF_3 \qquad Ici$$

wherein
Phe is a 1,4-phenylene group being unsubstituted or substituted by one or more halogen atoms or $CH_3$ or CN,
Dio is a 1,3-dioxane-2,5-diyl group,
Pyd is a pyridine-2,5-diyl group,
Pyr is a pyrimidine-2,5-diyl group,
Cyc is a 1,4-cyclohexylene group and
Che is a 1,4-cyclohexenylene group.

10. A liquid-crystalline phase according to claim 5, comprising at least one substituted phenyl trifluoromethyl ether of the sub-formulae Ida to Idk:

$$R^1-Phe-Z^1-Phe-Z^2-Phe-OCF_3 \qquad Ida$$

$$R^1-Phe-Z^1-Dio-Z^2-Phe-OCF_3 \qquad Idb$$

$$R^1-Cyc-Z^1-Cyc-Z^2-Phe-OCF_3 \qquad Idc$$

$$R^1-Pyd-Z^1-Phe-Z^2-Phe-OCF_3 \qquad Ide$$

$$R^1-Phe-Z^1-Pyd-Z^2-Phe-OCF_3 \qquad Idf$$

$$R^1-Pyr-Z^1-Phe-Z^2-Phe-OCF_3 \qquad Idg$$

$$R^1-Phe-Z^1-Pyr-Z^2-Phe-OCF_3 \qquad Idh$$

$$R^1-Phe-Z^1-Cyc-Z^2-Phe-OCF_3 \qquad Idi$$

| $R^1$—Dio—$Z^1$—Phe—$Z^2$—Phe—OCF$_3$ | Idj |
| $R^1$—Che—$Z^1$—Phe—$Z^2$—Phe—OCF$_3$ | Idk |

Phe is a 1,4-phenylene group being unsubstituted or substituted by one or more halogen atoms or CH$_3$ or CN,
Dio is a 1,3-dioxane-2,5-diyl group,
Pyd is a pyridine-2,5-diyl group,
Pyr is a pyrimidine-2,5-diyl group,
Cyc is a 1,4-cyclohexylene group and
Che is a 1,4-cyclohexenylene group.

11. A liquid-crystalline phase according to claim 5, comprising at least one substituted phenyl trifluoromethyl ether of the sub-formulae Iea to Iei:

| $R^1$—Pyr—$Z^1$—Phe—$Z^2$—Phe—OCF$_3$ | Iea |
| $R^1$—Dio—$Z^1$—Phe—Phe—OCF$_3$ | Ieb |
| $R^1$—Cyc—$Z^1$—Phe—Phe—OCF$_3$ | Iec |
| $R^1$—Phe—$Z^1$—Cyc—Phe—OCF$_3$ | Ied |
| $R^1$—Cyc—$Z^1$—Cyc—Phe—OCF$_3$ | Iee |
| $R^1$—Phe—$Z^1$—Dio—Phe—OCF$_3$ | Ief |
| $R^1$—Pyd—$Z^1$—Phe—Phe—OCF$_3$ | Ieg |
| $R^1$—Phe—$Z^1$—Pyr—Phe—OCF$_3$ | Ieh |
| $R^1$—Phe—$Z^1$—Che—Phe—OCF$_3$ | Iei | wherein
Phe is a 1,4-phenylene group being unsubstituted or substituted by one or more halogen atoms or CH$_3$ or CN,
Dio is a 1,3-dioxane-2,5-diyl group,
Pyd is a pyridine-2,5-diyl group,
Pyr is a pyrimidine-2,5-diyl group,
Cyc is a 1,4-cyclohexylene group and
Che is a 1,4-cyclohexenylene group.

12. A liquid-crystalline phase according to claim 5, comprising at least one substituted phenyl trifluoromethyl ether of the sub-formulae Ifa to Ifm:

| $R^1$—Pyr—Phe—$Z^2$—Phe—OCF$_3$ | Ifa |
| $R^1$—Pyr—Phe—OCH$_2$—Phe—OCF$_3$ | Ifb |
| $R^1$—Phe—Phe—$Z^2$—Phe—OCF$_3$ | Ifc |
| $R^1$—Cyc—Cyc—$Z^2$—Phe—OCF$_3$ | Ifd |
| $R^1$—Cyc—Cyc—CH$_2$CH$_2$—Phe—OCF$_3$ | Ife |
| $R^1$—Pyd—Phe—$Z^2$—Phe—OCF$_3$ | Iff |
| $R^1$—Dio—Phe—$Z^2$—Phe—OCF$_3$ | Ifg |
| $R^1$—Phe—Cyc—$Z^2$—Phe—OCF$_3$ | Ifh |
| $R^1$—Phe—Pyd—$Z^2$—Phe—OCF$_3$ | Ifi |
| $R^1$—Che—Phe—$Z^2$—Phe—OCF$_3$ | Ifj |
| $R^1$—Phe—Che—$Z^2$—Phe—OCF$_3$ | Ifk |
| $R^1$—Pyr—Phe—CH$_2$CH$_2$—Phe—OCF$_3$ | Ifl |
| $R^1$—Cyc—Phe—CH$_2$CH$_2$—Phe—OCF$_3$ | Ifm | wherein
Phe is a 1,4-phenylene group being unsubstituted or substituted by one or more halogen atoms or CH$_3$ or CN,
Dio is a 1,3-dioxane-2,5-diyl group,
Pyd is a pyridine-2,5-diyl group,
Pyr is a pyrimidine-2,5-diyl group,
Cyc is a 1,4-cyclohexylene group and
Che is a 1,4-cyclohexenylene group.

13. A liquid-crystalline phase according to claim 9, comprising at least one substituted phenyl trifluoromethyl ether which is:
trifluoromethoxy-4-[trans-4-(trans4-ethylcyclohexyl)-cyclohexyl]benzene,
trifluoromethoxy-4-[trans-4-(trans4-propylcyclohexyl)-cyclohexyl]benzene,
trifluoromethoxy-4-[trans-4-(trans-4-butylcyclohexyl)-cyclohexyl]benzene,
trifluoromethoxy-4-[trans-4-(trans-4-pentylcyclohexyl)-cyclohexyl]benzene,
trifluoromethoxy-4-[trans-4-(trans-4-hexylcyclohexyl)-cyclohexyl]benzene,
trifluoromethoxy-4-[trans-4-(trans-4-heptylcyclohexyl)-cyclohexyl]benzene,
trifluoromethoxy-4-[trans-4-(trans-4-octylcyclohexyl)-cyclohexyl]benzene,
trifluoromethoxy-4-[trans-4-(trans-4-nonylcyclohexyl)-cyclohexyl]benzene, or
trifluoromethoxy-4-[trans-4-(trans-4-decylcyclohexyl)-cyclohexyl]benzene.

14. A liquid-crystalline phase according to claim 6, comprising at least one substituted phenyl trifluoromethyl ether of the sub-formulae Io to Iv:

| $R^1$—Cyc—Cyc—Phe—Phe—OCF$_3$ | Io |
| $R^1$—Cyc—Cyc—$Z^1$—A$^2$—Phe—OCF$_3$ | Iq |
| $R^1$—A$^1$—A$^1$—A$^2$—CH$_2$CH$_2$—Phe—OCF$_3$ | Ir |
| $R^1$—Phe—$Z^1$—Phe—$Z^1$—Dio—Phe—OCF$_3$ | Is |
| $R^1$—Phe—$Z^1$—Phe—Phe—$Z^2$—Phe—OCF$_3$ | It | wherein
Phe is a 1,4-phenylene group being unsubstituted or substituted by one or more halogen atoms or CH$_3$ or CN,
Dio is a 1,3-dioxane-2,5-diyl group,
Cyc is a 1,4-cyclohexylene group.

15. A liquid-crystalline phase according to claim 1, comprising at least one substituted phenyl trifluoromethyl ether wherein
A$^3$ is a 1,4-phenylene group which is unsubstituted or substituted by one or two F atoms.

16. A liquid-crystalline phase according to claim 15, comprising at least one substituted phenyl trifluoromethyl ether of the sub-formulae 1 to 13:

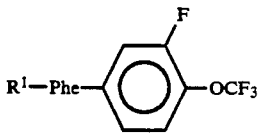

1

-continued
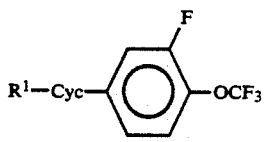 2
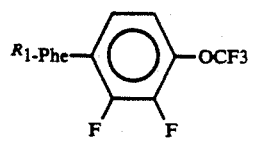 3
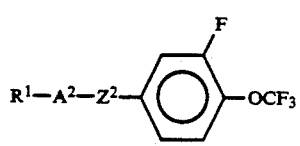 4
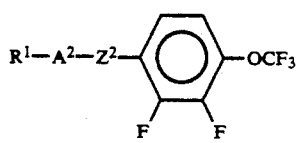 5
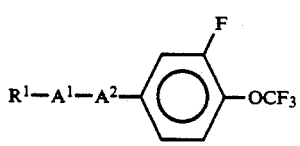 6
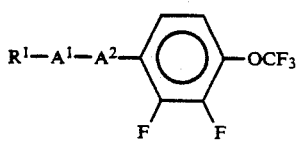 7
-continued
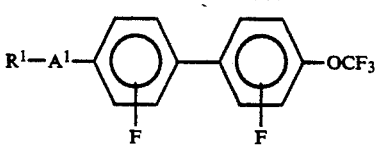 8
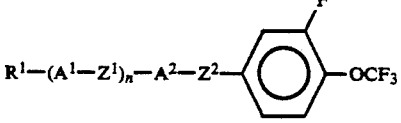 9
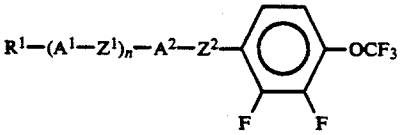 10
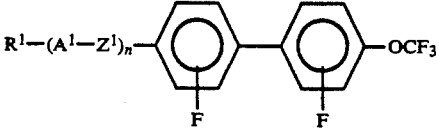 11
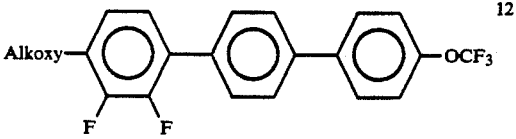 12
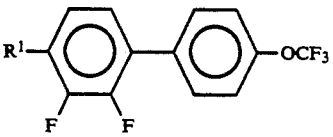 13
wherein Alkoxy is an alkoxy group with 2 to 9 C atoms.
* * * * *